United States Patent [19]

Eichardt et al.

[11] Patent Number: 5,408,316
[45] Date of Patent: Apr. 18, 1995

[54] ARRANGEMENT FOR ELECTROTHERMALLY ATOMIZING SPECIMENS TO BE ANALYZED

[75] Inventors: Klaus Eichardt, Jena, Germany; Bruno Hütsch, St. Vith, Belgium

[73] Assignee: Carl Zeiss Jena GmbH, Jena, Germany

[21] Appl. No.: 173,426

[22] Filed: Dec. 23, 1993

[30] Foreign Application Priority Data

Dec. 23, 1992 [DE] Germany ............ 42 43 766.0

[51] Int. Cl.$^6$ .............................................. G01N 21/74
[52] U.S. Cl. ........................................ 356/312; 356/244
[58] Field of Search .................................. 356/312, 244

[56] References Cited

U.S. PATENT DOCUMENTS

4,407,582  10/1983  Woodriff ............................. 356/312

FOREIGN PATENT DOCUMENTS

| | | |
|---|---|---|
| 0303134 | 2/1989 | European Pat. Off. . |
| 0311761 | 4/1989 | European Pat. Off. . |
| 0350722 | 1/1990 | European Pat. Off. . |
| 2323774 | 11/1974 | Germany . |
| 2148777 | 9/1975 | Germany . |
| 2413782 | 9/1975 | Germany . |
| 2718416 | 11/1978 | Germany . |
| 3228245 | 2/1983 | Germany . |
| 3442073 | 7/1985 | Germany . |
| 3534417 | 4/1987 | Germany . |
| 8714670 | 2/1988 | Germany . |
| 3735013 | 4/1989 | Germany . |
| 3802968 | 8/1989 | Germany . |
| 3924839 | 4/1990 | Germany . |
| 56-1338 | 1/1981 | Japan . |

OTHER PUBLICATIONS

"Neue Anwendungsmöglichkeiten der Graphitorhr-Atom-Absorptions-Spektroskopie durch den Einsatz von mikrocomputergesteuerten Programmern" by H. Schulze, GIT Fachz. Lab., Year 23, Jan. 1979.

*Primary Examiner*—F. L. Evans
*Attorney, Agent, or Firm*—Walter Ottesen

[57] ABSTRACT

The invention is directed to an arrangement for electrothermal atomization and includes a furnace body having a furnace tube defining a specimen chamber and defining a longitudinal tube axis and having two lateral sides extending parallel to the axis. The furnace body has two contact pieces formed on the furnace tube at corresponding lateral sides thereof. The contact pieces define a contact axis extending perpendicularly to the tube axis. The contact pieces and the furnace tube conjointly define a single integral body made of the same material. Each of the contact pieces includes raised portions defining furnace body contact surfaces. Two ring-shaped electrodes supply current to the furnace body and each of the electrodes defines an electrode contact surface for contact engaging the contact surfaces of one of the contact pieces thereby establishing an electric contact interface to the one contact piece. The two electrodes and the furnace body are configured so as to cause the electric contact interfaces to be the electrical contacts to the furnace body. A separate hollow body is interposed between the two electrodes and has an interior for accommodating the furnace tube therein. The hollow body includes a first passage for facilitating placing a specimen in the specimen chamber and a second passage for conducting protective gas to the furnace body and a third passage facilitates radiating a measuring light beam through the specimen chamber.

38 Claims, 5 Drawing Sheets

ARRANGEMENT FOR ELECTROTHERMALLY ATOMIZING SPECIMENS TO BE ANALYZED

BACKGROUND OF THE INVENTION

Arrangements for electrothermally atomizing analysis specimens are known as graphite furnaces in the area of atomic absorption spectroscopy. The graphite furnaces always essentially comprise a furnace body which is disposed in a protective gas atmosphere between two electrodes as disclosed in German patent publication 2,413,782. The furnace body is often configured as a graphite tube and is referred to as such and the electrodes are configured as graphite housing parts. The electrodes are usually held in water-cooled metal jackets and are connected via these jackets to a controllable current source. The furnace body, and therefore the specimen to be analyzed, is electrothermally heated with the aid of a time-controlled high current conducted through the cross section of the furnace body. The specimen to be analyzed is converted into free atoms as completely as possible in the inner chamber of the furnace body. The free atoms can be optically detected. The effectiveness of the atomization is essentially determined by the speed of the temperature heating process and the quality of the transfer to an isotropic temperature distribution in the interior chamber of the furnace body which is necessary for the atoms to be determined. The process of generating and of the residence (breakdown) of the free atoms is generally known as the atomizing phase and includes a typical time duration of 1 to 10 seconds in dependence upon the element to be determined and on the quantity of the analyte. The atomizing temperatures necessary for the specific element extend over a range of 800° to 2800° C. The temperature is the most essential parameter determining the quality criteria, the detection capability and the reproducibility for the atomization process with the electrothermally heated furnace body. Generally, an isotropic temperature distribution in the entire furnace body cannot be assumed. A furnace body temperature at a specific time point requires the availability of a specific electric power. Characteristics of the furnace body, on the one hand, such as material characteristics, mass and geometric form as well as, on the other hand, characteristics of the graphite oven sleeve in contact with the furnace body have a complex influence on the particular furnace body temperature which is adjusted and finally on the electric power necessary for generating this temperature. The characteristics of the graphite oven sleeve include the contacting and heat transfer of the cooling, radiation feedback of the surrounding inner surface of the graphite furnace and the means for conducting the protective gas.

The furnace body temperature is essentially determined by the difference of heat quantity from the heat generated by the supplied current and the heat losses flowing away via the furnace contacts in the range of room temperature to approximately 1000° C. On the other hand, above 1500° C. (increasing proportionally to the fourth power of the temperature), the difference of the generated heat and the loss quotient of heat radiating from the furnace body and the heat radiated back from the interior of the furnace is more significant.

Graphite furnaces have been known in the state of the art for approximately 20 years and have a tube-shaped furnace body with the following dimensions: 20 to 40 mm length, 3 to 6 mm inner diameter and 0.5 to 1.5 mm wall thickness. These graphite furnaces are known as graphite tubes and are usually held at their ends in cooled ring-shaped contacts. The graphite tubes are flushed within and without with flows of protective gas and are enclosed in furnace housing parts defining a hollow chamber. The housing parts are electrically insulated with respect to each other. The delivery channel for the specimen to be analyzed and a gap-like interface in the furnace housing are the only openings of this kind for a half-closed graphite furnace arrangement which is known also as a Massmann furnace. A significant disadvantage of this arrangement is that a temperature gradient of several hundred degrees is formed by the heat flowing off via the furnace body ends. This characteristic leads to the deterioration of the effectiveness of the atomization and to analytic disturbances because of condensation processes of the analyte components previously vaporized in the heating phase at the cooled furnace body ends. Furnace arrangements of this kind are disclosed, for example, in published German patent application 2,413,782.

Graphite furnace arrangements of the Massmann type having a more uniform temperature distribution along the tube axis as compared to the previously described arrangement are obtainable by means of a cross section profile of the tube wall thickness. Different variations are known wherein the tube body exhibits a reduced electrical conductivity especially in the vicinity of its contacts. The temperature drop because of a flow of heat to the contacts essentially remains but the zone of isotropic temperature relationships starting at the tube center is expanded. Examples of the foregoing are provided in German patent publications 3,228,245; 3,442,073; and 2,148,777.

It is furthermore known that an isotropic temperature distribution along the furnace body axis is then obtained if the heating current is conducted in the peripheral direction of the furnace body transversely to the tube axis. This temperature distribution is better suited to the analytic requirements of the electrothermal atomization. Two so-called open graphite furnace arrangements are disclosed in U.S. Pat. 4,407,582 wherein one pair or two pairs of bifurcated contact pieces are in contact engagement radially on mutually opposite sides of the tube-shaped furnace body. Significant disadvantages of these arrangements are: the poor contact at the hot outer surface of the furnace body, the isotropic temperature relationships only in the region of the contact locations and the missing protective sleeve in the form of a furnace housing as protection against effects of atmospheric oxygen.

Configurations of a tube-shaped graphite furnace body having diagonally opposite-lying contact pieces are known as "Frech-Hütsch cuvettes". The contact pieces are formed on the outer surface on the longitudinal sides of the tube axis. In this connection, reference may be made to published German utility model registration 8,714,670 and German patent publication 3,534,417.

Different geometric modifications for influencing the furnace body temperature are described.

These configurations are only useful to a limited extent since no solutions are offered for the configuration of graphite furnace arrangements on the basis of transversely heated cuvettes for the complex exchange effect problems which occur thereby. The described geometric variations have no isotropic current density and therefore no isotropic temperature relationships over the length of the tube outer surface.

The configuration of a graphite furnace arrangement for a tube-shaped, transversely-heated furnace body having diametrically opposite lying contact pieces is disclosed, for example, in European patent publications 0,350,722; 0,303,134; and, 0,311,761 as well as in published German patent publications 3,802,968 and 3,735,013. A furnace body is described having a geometry which is complicated to manufacture and therefore is of high cost to the user as a part subject to wear. The furnace body is held between two large cylindrical contacts defining a cylindrical hollow chamber so that it can be flushed with a protective gas flow and is enclosed by the two contacts which conjointly define an annular gap therebetween. The heat balance and heat distribution of the tube-shaped furnace body part of this graphite furnace arrangement are not isotropic along the length of the tube axis and especially during the usual heating time of approximately 1 second of the atomizing step and the holding phase of several seconds which follows. The contact pieces have a trapezoidal shape when viewed in plan and are formed on the tube-shaped furnace body. The contact pieces have several breakthroughs and constrictions on the longitudinal side of the tube outer surface so that a constant current density distribution is not provided and therefore also a constant generation of heat and removal of heat over the tube length are not provided. Furthermore, the circularly-shaped configuration of the electrode inner wall over the longitudinal tube axis leads to nonuniform heat losses because of nonuniform interaction of radiation between furnace body surface and inner chamber wall. This increases with temperatures above 1500° C. with the loss components on the tube-body ends being significantly higher than at the tube center.

The contact projections are large and are held relatively cold. These projections have a large heat capacity so that the actual furnace body can only then maintain a temperature level obtained at the end of the heating phase when the heat loss which occurs immediately because of the thermal balancing processes is compensated by a complex control algorithm for the heat capacity. Otherwise, considerable losses of analyte atoms would occur because of the immediate drop of the furnace body temperature.

The contact surfaces are configured to be small with respect to area and are between the two contacts and the furnace body contact pieces and lead to local overheating and power losses and overall to an unstable contact and temperature performance. This is caused by the heating rate required for an effective atomization which is up to 2000 kelvin per second and by the necessary current intensities of approximately 1000 ampere (effective).

SUMMARY OF THE INVENTION

It is an object of the invention to provide a new arrangement for electrothermal atomization which simultaneously affords the advantages of a longitudinally heated furnace arrangement of the Massmann type. It is also an object of the invention to provide this new arrangement based on the transversely-heated furnace body base form.

The components of the overall arrangement are intended to coact so that:

(a) the tube-shaped part of the furnace body exhibits isotropic temperature relationships over its entire length during any desired heatup and holding phases;

(b) the thermal capacities of individual parts of the arrangement and especially of the contact pieces of the furnace body are so matched to each other that any desired temperature-time trace can be adjusted within analytically relevant limits in accordance with a sensorless control model of the temperature-time trace of the furnace body in accordance with previously determined electrical and thermal parameters of the system on an adaptive control basis with the parameters being stored in a computer;

(c) the expendable parts such as furnace body and specimen input funnel are simple to manufacture and therefore have cost-effective geometries and are simple to exchange;

(d) protective gas flows are formed which are independent of each other and which are symmetrical to the center of the furnace body. An effective rinsing of the furnace window and a rapid and reliable removal of thermal decomposition products of the sample are ensured;

(e) an effective protection against the effects of atmospheric oxygen with a small consumption of protective gas is provided; and, (f) the cooling time of the arrangement and therefore the maximum possible throughput of the specimen does not differ significantly from the longitudinally-heated graphite furnaces (that is, less than 30 seconds).

The arrangement of the invention is for electrothermal atomization and includes: a furnace body having a furnace tube defining a specimen chamber and defining a longitudinal tube axis and having first and second lateral sides extending parallel to the axis; the furnace body having first and second contact pieces formed on the furnace tube at corresponding ones of the first and second lateral sides; the first and second contact pieces defining a contact axis extending perpendicularly to the tube axis; the furnace body having a predetermined longitudinal length and the contact pieces extending over the length and the furnace tube and the contact pieces conjointly defining a single integral body made of the same material; each of the contact pieces having a parallelepiped-like shape uninterrupted by breakthroughs and having substantially rectangular end faces defining two corner regions; each of the contact pieces further including raised portions formed at corresponding ones of the corner regions thereof; the raised portions defining furnace body contact surfaces facing away from the contact piece; first and second ring-shaped electrodes for supplying current to the furnace body; each of the electrodes defining an electrode contact surface for contact engaging the furnace body contact surfaces of one of the contact pieces thereby establishing an electric contact interface to the one contact piece; the first and second electrodes and the furnace body being configured so as to cause the electric contact interfaces to be the electrical contacts to the furnace body; a separate hollow body interposed between the first and second electrodes and having an interior for accommodating the furnace tube therein; the hollow body including first passage means for facilitating placing a specimen in the specimen chamber; second passage means for conducting protective gas to the furnace body; and, third passage means for facilitating radiating a measuring light beam through the specimen chamber; and, the hollow body and the first and second electrodes being configured and disposed so as to conjointly surround the furnace body.

The conditions formulated in the above objects are realized with the above features of the invention. Heat losses are small which occur especially because of the configuration of the furnace body. These heat losses are constant and are held so that they are detectable in order to configure the entire arrangement so as to be electrically controllable without it being necessary to use complicated furnace body geometries.

At the same time, this means that the simple geometry of the furnace body permits a cost-effective exchange of this main expendable part of the arrangement for the user.

The furnace body with the furnace and contact housing configured in accordance with the invention as well as the special form of the protective gas supply define a functional unit which is matched with respect to its specific operations.

The configuration of form and size of the contact pieces and the form of the electrodes matched thereto can markedly reduce the pressing force while providing constant contact resistances (especially the configuration of the conical angle of the cones near the self-holding limit of two mutually engaging conical segments). The above configuration of form and size of the contact pieces significantly increases the service life of the furnace body used since the danger of breaking at the location of narrow cross sections is reduced.

In contrast to previous solutions, the contact pieces are not held together over their longitudinal surfaces in the manner of a vise. For this reason, a simple pivoting away of one of the electrodes of the furnace body provides access in order to exchange the furnace body. The electrode is surrounded, for example, by a pivotable cooling jacket.

The hollow part is configured as a separate unit between the electrodes. For this reason, an exchange of this part can take place without it being necessary to exchange the electrodes themselves. This part is subjected to intense wear because of chemical and thermal loads.

The hollow part simultaneously performs several functions: supplying protective gas flows to the furnace body; accommodating an exchangeable specimen channel; and, accommodating the holding parts for the optical cuvette windows.

A seam is provided between the hollow part and the ring-shaped electrode which can also contain an air gap. Because of this seam location, the thermal flow to the electrode is interrupted; that is, the thermal flow takes place only via the holder of the hollow part so that the operating temperature of the hollow part is increased in a desired amount. The hollow part itself can be made of a material of the group of ceramic materials or hydrocarbons or graphite.

BRIEF DESCRIPTION OF THE DRAWINGS

The invention will now be described with reference to the drawings wherein:

FIG. 2 is a section view taken through the furnace body of

FIG. 1 along the contact axis thereof;

DESCRIPTION OF THE PREFERRED EMBODIMENTS OF THE INVENTION

Figure 1:
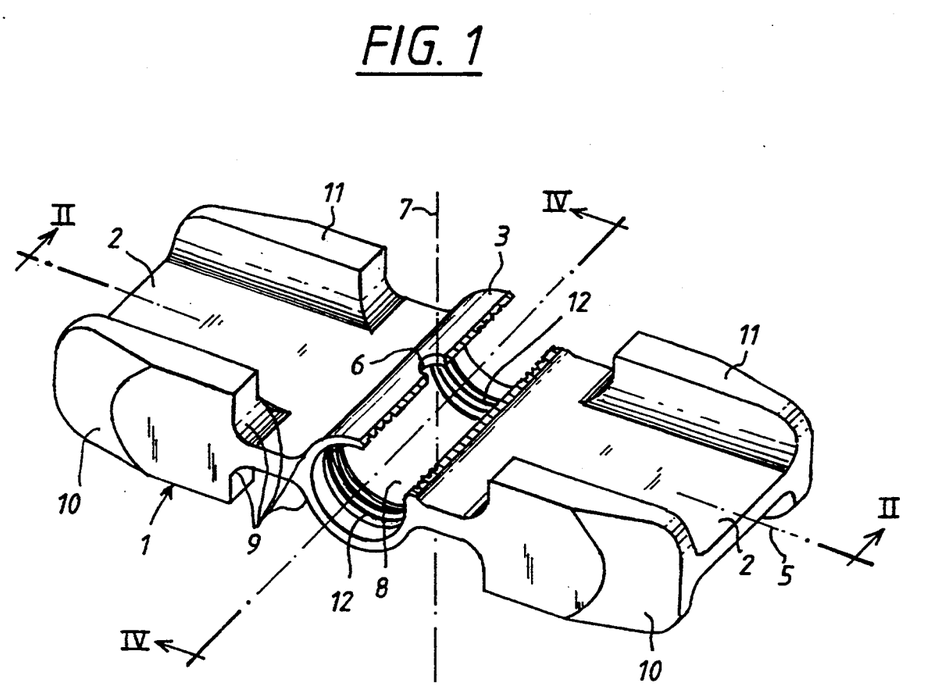
FIG. 1 is a perspective view of a tube-shaped furnace body according to a feature of the invention with a portion of the furnace tube broken away.

A tube-shaped furnace body 1 is shown in FIG. 1 and is a graphite part having a base form corresponding to a parallelepiped with beveled corner surfaces. A symmetrically configured tube 3 of the furnace body 1 preferably has a hollow cylindrical shape. The shape of the tube 3 is, however, not limited to a cylindrical form. Annular members having a cornered or other cross sections are also possible.

The intersect point of three mutually perpendicular axes is at the geometric center of the furnace body 1. These axes are: the longitudinal tube axis 4, the contact axis 5 running in the direction of the contact pieces 2 extending from the tube 3 and the specimen channel axis 7 running through the specimen input opening 6.

The actual atomizer chamber for the specimen to be analyzed is defined by the interior space 8 of the tube 3.

Figure 2:
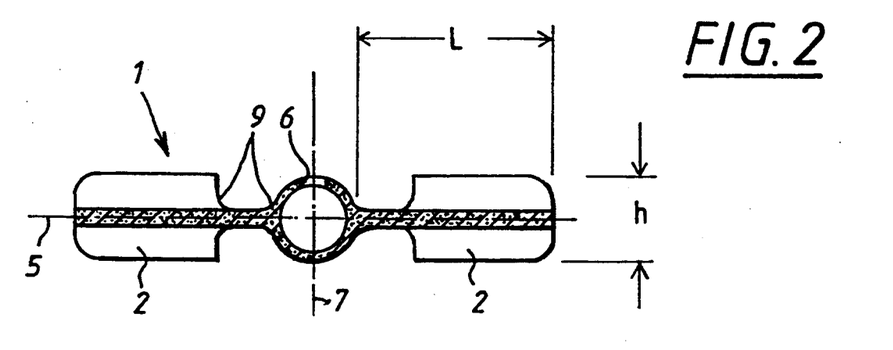
Figure 3:
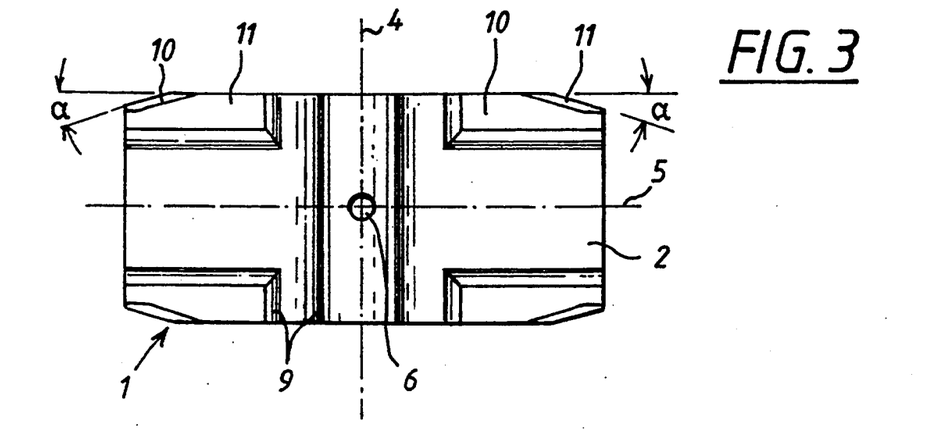
FIG. 3 is a plan view of the furnace body of FIG. 1.

The contact pieces 2 have a contact piece length L and are formed on the outer surface of the tube 3 so as to lie diametrically opposite each other. The contact pieces 2 define respective curved surfaces 9. Raised portions 11 are formed on the longitudinal sides of the contact pieces. These raised portions increase the thickness of the contact pieces in the region of the corner surfaces 10 symmetrically to the contact axis 5. The elevation h of the raised portions 11 preferably corresponds to the outer diameter of the tube 3 as shown in FIG. 2. The corner surfaces 10 extend over the cross section of the raised portions 11 and are configured as conically-shaped segment pairs at a conical angle $\alpha$ close to the self-holding limit of two graphite cones placed one inside the other. The conical angle $\alpha$ is in the range of 20° to 40° and is preferably 30°.

Figure 4:
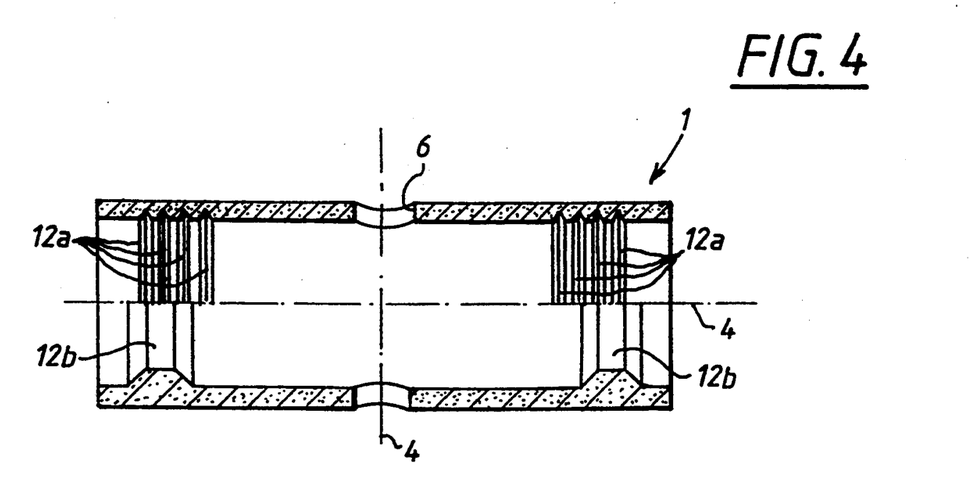
FIG. 4 is a section view through the furnace body along the longitudinal tube axis.

The enlargement of the corner surfaces 10 of the contact pieces 2 results from the conical angle $\alpha$ and the cross-sectional elevation h of the raised portions.11. The enlargement of the corner surfaces 10 of the contacts pieces 2 is at a ratio of 4:2:1 with respect to the cross section in the unthickened area of the contact piece and to the wall thickness cross section of the tube 3. However, other surface ratios in the tube 3 also permit an approximately linear temperature gradient to be realized. The interior space 8 of the tube 3 has at least one groove-shaped hindrance 12a which prevents the spread of a liquid specimen in the direction of the tube ends. The groove-shaped hindrances 12a are shown in the partial section view of FIG. 1 and in FIG. 4 and are at the same distance from the respective longitudinal tube ends. The groove 12a can extend about the periphery as well as also only over a part of the inner periphery of the tube-shaped furnace body.

An internal ring arranged at both ends such as a raised circular ring 12b can be used in lieu of the grooves 12a shown. The raised ring 12b is shown in the lower half of FIG. 4. The raised portion can be a raised segment of a circular ring extending over only portion of the inner periphery of the furnace tube.

The ratio of the width of each raised portion 11 to the width of the furnace body 1 measured in the direction of the longitudinal tube axis 4 is 1:5 and, the ratio of the length of each raised portion 11 measured in the direction of the contact axis 5 is at most ⅔ of the length L of the contact piece 2.

Figure 5:
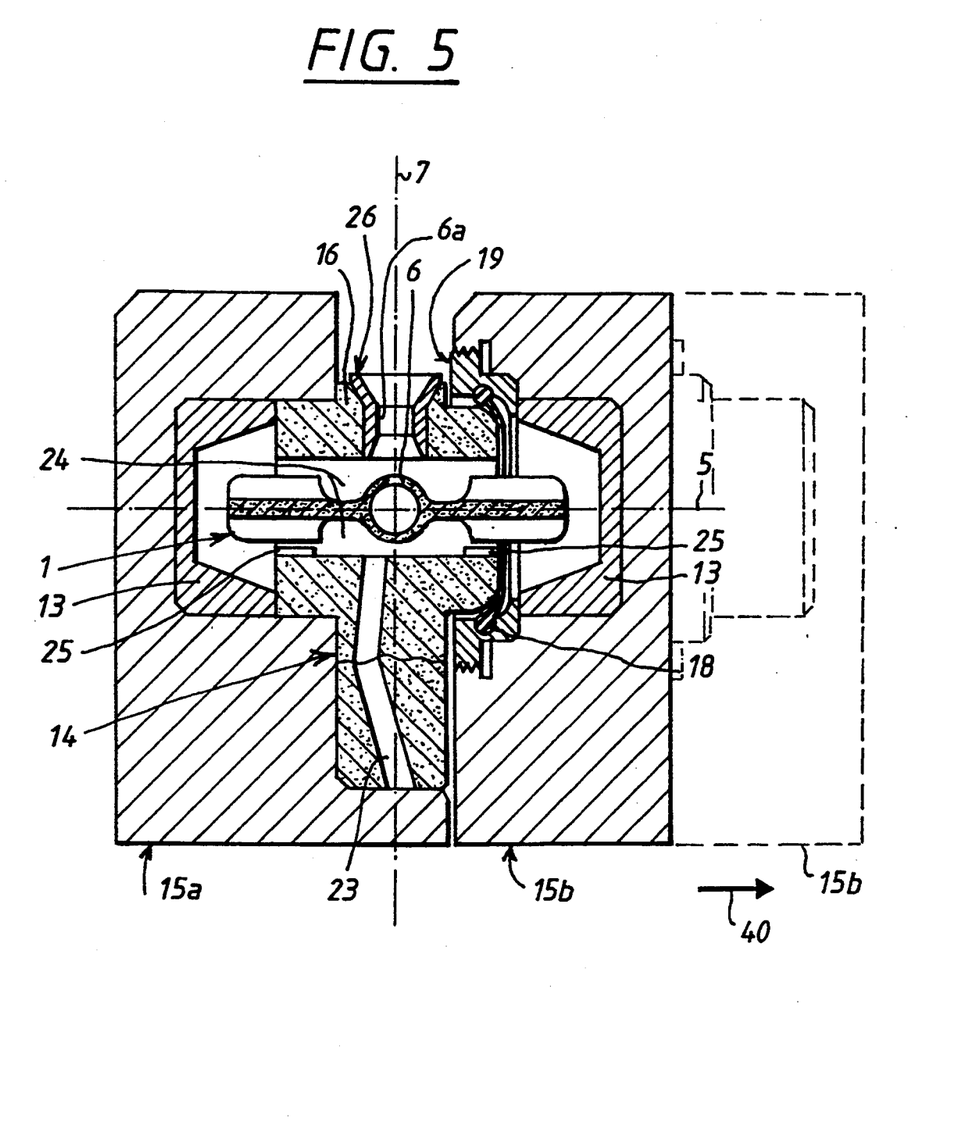
FIG. 5 is a section view through the complete arrangement according to the invention taken along the contact axis of the furnace body.
Figure 6:
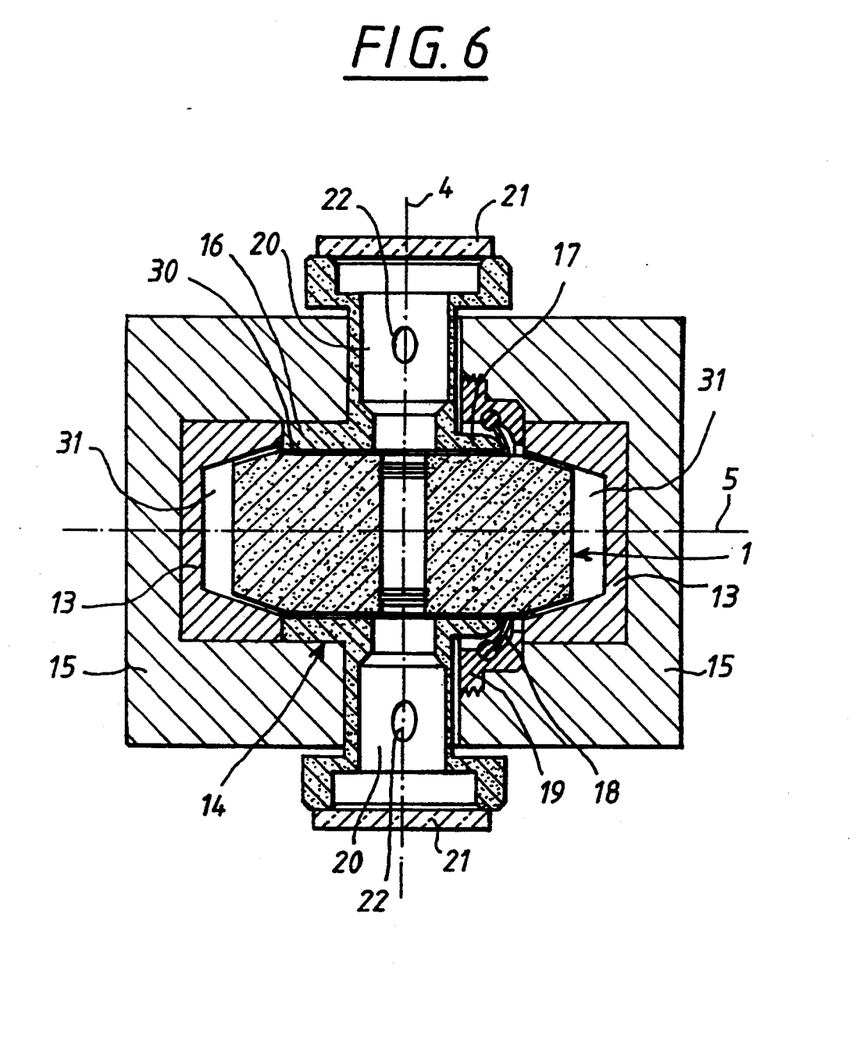
FIG. 6 is a section view also taken through the contact axis but at 90° with respect to the section view of FIG. 5; and, FIG. 7 is a section view taken along the specimen channel axis to show the gas channels and the inner space of the furnace.
Figure 7:
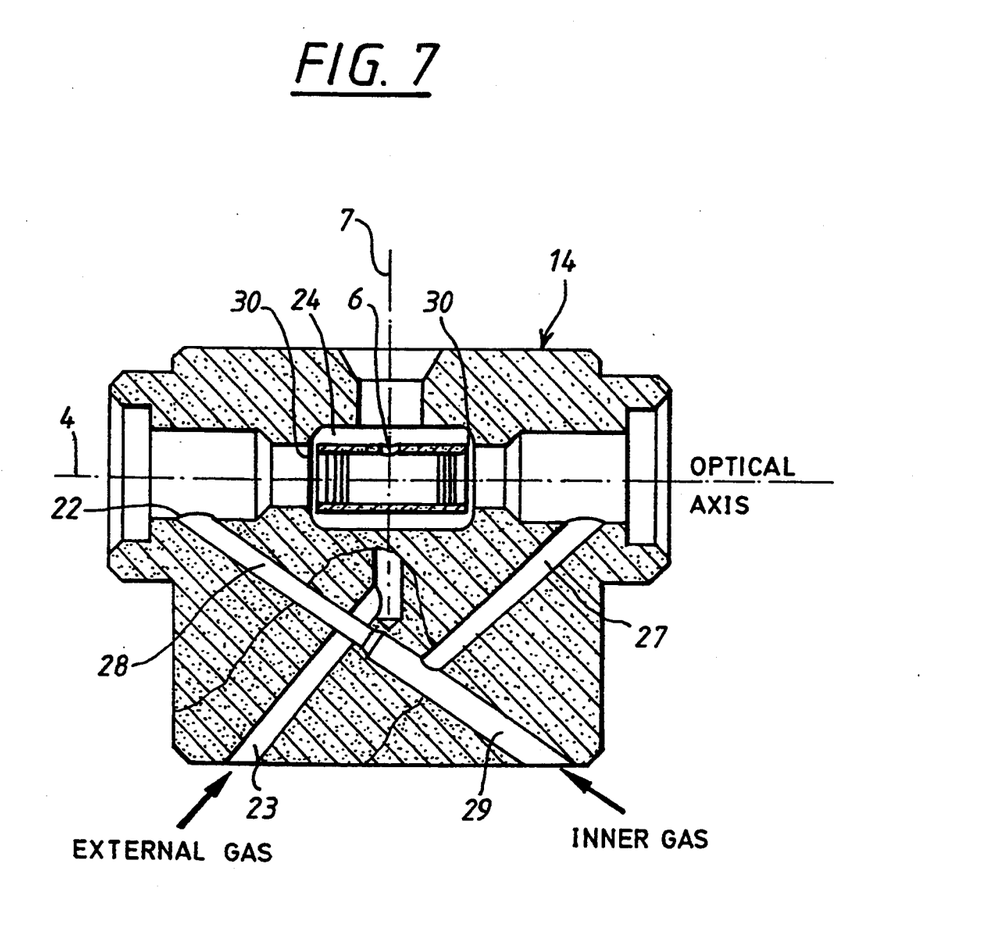

The overall arrangement according to the invention is shown in FIGS. 5 to 7.

The tube-shaped furnace body 1 engages via the corner surfaces 10 in complementary, cone-shaped inner surfaces of the ring-shaped electrodes 13. Each of the contact pieces 2 extend into the electrode 13 corresponding thereto to an extent corresponding to approximately ⅓ of the length L to the contact piece. The corner surfaces 10 of each contact piece 12 are in contact engagement with the cone-shaped inner surface of a recess of a corresponding one of the electrodes 13. This surface-to-surface contact provides a constant electrical contact.

The electrodes 13 together with a hollow part 14 completely enclose the furnace body 1. The hollow body 14 encloses portions of the contact pieces 2 constituting 50 to 70% thereof measured in the direction of the contact axis 5. The ring-shaped electrodes 13 and partially the hollow part 14 are surrounded by cooling jackets (15a, 15b) which are preferably made of metal. One of the cooling jackets 15b is drawn in phantom outline in FIG. 5 to show how this jacket moved away in the direction of arrow 40.

Two cylindrical hollow shafts (16, 17) are formed on the hollow part 14 as shown in FIG. 6. These cylindrical hollow shafts (16, 17) extend in the direction of the contact axis 5. The shaft 16 extends with its end face to a ring-shaped electrode 13 and is surrounded by a cooling jacket 15a. The opposite-lying shaft 17 has a conically-shaped outer surface which is in contact with the sealing lip of a flexible sealing ring 18 which is held in a carrier ring 19 surrounded by the cooling jacket 15b.

Two further cylindrical hollow shafts 20 are formed in the hollow part 14 and extend in the direction of the longitudinal tube axis 4. The hollow shafts 20 serve to lead in and lead out the measuring light beam (not shown) into the inner space 8 of the tube 3 via window 21 so that the tube axis 4 is also the optical axis. Outlet openings 22 of the channels (27, 28) open into the hollow shafts 20. The channels (27, 28) are shown in FIG. 7 and are provided for conducting the interior component gas flows.

The channel 23 for the external protective gas flow is shown in the section view of FIG. 5. The channel 23 opens into the interior space 24 of the graphite hollow part 14 below the tube 3.

The interior space 24 has a generally parallelepiped shape and includes support points 25 for preadjusting the position of the furnace body 1 by means of its own weight when the arrangement is open.

When closing the arrangement, the contact pieces 2 slide on the corner surfaces 10 into the ring-shaped electrodes 13 and the furnace body 1 is simultaneously raised until it is at the elevation of the tube axis 4.

A funnel part 26 has a specimen opening 6a for introducing the specimen is provided above the specimen input opening 6 in tube 3. The funnel part 26 can be exchanged and is configured, for example, as a graphite form part coated with pyrocarbon material. The funnel part 26 extends in the direction of the specimen channel axis 7 (see FIG. 5). In this way, the regular cleaning to avoid contamination is ensured.

The channels 27 and 28 shown in FIG. 7 are provided for the inner component gas flows and are provided preferably by a 1:1 split-up of a common feed channel 29 and open in outlet openings 22. The internal gas flow is represented schematically by arrow 42.

The channel 23 is provided for the external protective gas flow and is shown only partially in the section view of FIG. 7. The external gas flow is represented schematically in FIG. 7 by arrow 44.

The furnace body 1 is so positioned in the parallelepiped interior space 24 that gaps 30 having essentially constant widths are provided on both sides between the outer surface of the tube 3 and the inner wall of the inner space 24. The gap 30 has a width in the range of 0.5 to 1.0 mm.

The contact pieces 2 are formed on the tube 3 and exhibit no breakthroughs or additional constrictions in the region where the contact pieces 2 are formed on the tube so that a completely homogeneous current density distribution over the contact piece cross section and therefore also in the tube cross section is provided as a precondition for the generation of joulean heat.

The large-area corner surfaces 10 are arranged in pairs at the ends of the contact pieces 2 and ensure that the supply of current is reproducible and ensure a constant heat dissipation.

In this way, regions of approximately linearly increasing temperature gradients are formed within the cross section of the contact pieces 2 which start from the contact surfaces 10 and extend to the outer surfaces of the tube 3.

This leads to an only insignificant dissipation of heat from the tube 3 into the contact pieces 2 which is of special significance for the analytically relevant transition phase from the heat-up step to the holding step in the atomization phase. At the same time, it is ensured that the loss factor through heat dissipation on the total heat balance of the furnace body is approximately constant within the analytic constant temperature range. This effect could not be attained with a known cuvette such as of the "Frech-Hütsch" type discussed initially above.

The rectangular configuration of the cross section of the inner space 24 shown in FIGS. 5 and 7 guarantees that each point of the surface lines of the tube 3 in the direction of the longitudinal tube axis 4 is at a constant geometric spacing to the inner wall of the hollow part 14, whereby the heat loss because of the interaction of radiation between the tube surface and the interior space is held essentially constant.

At the same time, the constant dimensions of the gaps (30, 31) ensure a defined flow of protective gas.

The channelling of the outer and inner protective gas flows is provided as described below.

The inner component gas flows of the channels (27, 28) are directed toward the centers of the windows 21 and flush the inner sides of the windows 21 and thereafter flow in the direction of the center of the tube 3. A further defined division of the component gas flows takes place at the gap 30 between the tube ends and the inner space 24 before these component gas flows recombine over the tube 3 after completely flushing the tube body inside and out and thereafter exit from the funnel part 26.

The outer protective gas flow which flows out of the channel 23 fills the component space below the furnace body 1 at first completely before it flushes the furnace body 1 via the gaps (30, 31) surrounding the furnace body and flows into the component space above the furnace body 1 and likewise leaves the inner space 24 via the funnel part 26.

In addition to the complete flushing on all sides of the furnace body 1, the channelling of the inner component gas flows facilitates a rapid removal of specimen residues from the tube inner space 8 in the thermal decomposing phase of the specimen to be analyzed. The residence time of the analyte atoms formed in the tube can be positively influenced by varying the quantity of gas.

The furnace body 1 expands thermally during the heat-up process of this furnace body with the thermal expansion preferably being in the direction of the contact axis 5 whereby the spacing between the end face of the hollow part 14 and the carrier ring 19 is increased.

The sealing lip of the seal ring 18 moves with this expansion thereby preventing the entry of atmospheric oxygen into the inner space 24.

It is understood that the foregoing description is that of the preferred embodiments of the invention and that various changes and modifications may be made thereto without departing from the spirit and scope of the invention as defined in the appended claims.

What is claimed is:

1. An arrangement for electrothermal atomization, the arrangement comprising:

a furnace body having a furnace tube defining a specimen chamber and defining a longitudinal tube axis and having first and second lateral sides extending parallel to said axis;

said furnace body having first and second contact pieces formed on said furnace tube at corresponding ones of said first and second lateral sides;

said first and second contact pieces defining a contact axis extending perpendicularly to said tube axis;

said furnace body having a predetermined longitudinal length and said contact pieces extending over said length and said furnace tube and said contact pieces conjointly defining a single integral body made of the same material;

each of said contact pieces having a parallelepiped-like shape uninterrupted by breakthroughs and having substantially rectangular end faces defining two corner regions;

each of said contact pieces further including raised portions formed at corresponding ones of the corner regions thereof;

said raised portions defining furnace body contact surfaces facing away from the contact piece;

first and second ring-shaped electrodes for supplying current to said furnace body;

each of said electrodes defining an electrode contact surface for contact engaging the furnace body contact surfaces of one of said contact pieces thereby establishing an electric contact interface to said one contact piece;

said first and second electrodes and said furnace body being configured so as to cause the electric contact interfaces to be the electrical contacts to said furnace body;

a separate hollow body interposed between said first and second electrodes and having an interior for accommodating said furnace tube therein;

said hollow body including first passage means for facilitating placing a specimen in said specimen chamber; second passage means for conducting protective gas to said furnace body; and, third passage means for facilitating radiating a measuring light beam through said specimen chamber; and, said hollow body and said first and second electrodes being configured and disposed so as to conjointly surround said furnace body.

2. The arrangement of claim 1, wherein said raised portions are respective conical segments with said furnace body contact surfaces defining a conical angle $\alpha$; said electrode contact surface and the corresponding electrode being complementary to said contact surfaces; and, the cross section of each of said contact pieces being increased in the region of each raised portion.

3. The arrangement of claim 2, wherein said conical angle $\alpha$ is in the range of 20° to 40°.

4. The arrangement of claim 2, wherein the ratio of the width of each raised portion to the width of said furnace body measured in the direction of said longitudinal tube axis is 1:5; and, the ratio of the length of each raised portion measured in the direction of said contact axis being at most $\frac{2}{3}$ of the length (L) of the contact piece.

5. The arrangement of claim 2, wherein each of said raised portions has an elevation (h) equal to the outer diameter of said furnace tube.

6. The arrangement of claim 1, wherein the furnace body contact surfaces of each contact piece have a total surface area which is at a ratio to the cross section of the contact piece and to the cross section of the wall of the furnace tube of 4:2:1.

7. The arrangement of claim 1, wherein the transition of the contact piece per se to said raised portions and to said furnace tube is characterized by curved surfaces to prevent the formation of fissures at the transitions.

8. The arrangement of claim 1, said furnace tube having an inner wall surface and said furnace tube including first and second hindrance means formed in said inner wall surface at equal distances from the longitudinal ends of said tube to prevent a liquid analysis specimen from escaping from the specimen chamber.

9. The arrangement of claim 8, each of said hindrance means being a groove.

10. The arrangement of claim 9, each of said grooves extending only over a portion of the inner periphery of said furnace tube.

11. The arrangement of claim 8, each of said hindrance means being a raised circular ring on said inner wall surface.

12. The arrangement of claim 8, each of said hindrance means being a raised segment of a circular ring extending over only a portion of the inner periphery of said furnace tube.

13. The arrangement of claim 1, further comprising first and second cooling jackets completely surrounding corresponding ones of said first and second electrodes.

14. The arrangement of claim 1, each of said contact pieces extending into the electrode corresponding thereto to an extent corresponding to approximately $\frac{1}{3}$ of the length L of the contact piece.

15. The arrangement of claim 1, each of said electrodes having the same geometric form.

16. The arrangement of claim 1, said hollow body enclosing said furnace tube and at least portions of said contact pieces symmetrical to said tube axis.

17. The arrangement of claim 16, said hollow body enclosing portions of said contact pieces constituting 50 to 70% thereof measured in the direction of said contact axis.

18. The arrangement of claim 1, said interior of said hollow body having a rectangular cross section when viewed in a section plane containing said contact axis and perpendicular to said tube axis.

19. The arrangement of claim 18, said hollow body having an inner wall defining said interior; said furnace body and said inner wall conjointly defining a gap therebetween to prevent unwanted electrical and thermal contact between said furnace body and said inner wall; and, said second passage means defining an opening communicating with said interior and said gap also being provided to allow said protective gas to flow therethrough.

20. The arrangement of claim 19, said gap having a constant gap width and being in the range of 0.5 to 1.0 mm.

21. The arrangement of claim 19, further comprising two opposite-lying contact points formed in said inner wall for preadjusting the position of said furnace body by its own weight.

22. The arrangement of claim 19, said hollow body having a parallelepiped shape and being made of graphite; said hollow body having first and second cylindrical hollow shafts formed thereon on opposite sides thereof; and, said hollow shafts conjointly defining an axis of symmetry intersecting the center point of said furnace body.

23. The arrangement of claim 22, said axis of symmetry being coincident with said contact axis.

24. The arrangement of claim 23, said third passage means including first and second hollow shafts in said hollow body arranged along said tube axis for permitting said measuring light beam to pass through said specimen chamber; and, first and second receiving surfaces formed on said hollow body at said first and second hollow shafts for receiving respective cuvette windows.

25. The arrangement of claim 22, said first cylindrical shaft having an end face for contact engaging said first electrode.

26. The arrangement of claim 25, further comprising a first metal cooling jacket having a cylindrical recess completely surrounding said first cylindrical shaft and said first electrode.

27. The arrangement of claim 26, said second hollow shaft having an end face and having a conically-shaped outer surface extending to said end face; the arrangement further comprising a second metal cooling jacket; a carrier mounted in said second metal cooling jacket and a lip seal held in said carrier so as to be in contact engagement with said conically-shaped outer surface; and, said carrier and said hollow body conjointly defining a gap therebetween.

28. The arrangement of claim 27, said second metal cooling jacket being movable so as to allow access to said furnace body.

29. The arrangement of claim 24, said first and second hollow shafts having a stepped configuration.

30. The arrangement of claim 22, said furnace tube having a specimen input opening formed therein; and, said first passage means including a specimen input passage formed in said hollow body which is in alignment with said specimen input opening.

31. The arrangement of claim 30, further comprising an exchangeable funnel insertable into said specimen input passage.

32. The arrangement of claim 31, said funnel being a molded graphite part coated with pyrocarbon.

33. The arrangement of claim 1, said second passage means including an opening formed in said hollow body in said interior for allowing the protective gas to escape from said interior.

34. The arrangement of claim 24, said second passage means comprising first channel means formed in said hollow body for conducting internal protective gas and second channel means formed in said hollow body for conducting external protective gas; said first channel means defining first and second outlets in said interior forward of said cuvette windows.

35. The arrangement of claim 34, said first and second channel means having respective openings on the lower side of said interior.

36. The arrangement of claim 34, said first channel means having a main channel formed in said hollow body and first and second branch channels in said hollow body leading to said first and second outlets, respectively.

37. The arrangement of claim 36, said first and second branch channels defining respective longitudinal axes extending in respective directions so as to intersect with said tube axis at corresponding ones of said cuvette windows.

38. The arrangement of claim 34, said gap being a first gap and said first and second contact pieces and said first and second ring-shaped electrodes conjointly defining respective second gaps; said furnace tube having respective longitudinal end faces; said inner wall of said hollow body and said end faces conjointly defining respective third gaps; said furnace tube having a specimen input opening formed therein; said first passage means including a specimen input passage formed in said hollow body which is in alignment with said specimen input opening; a funnel mounted in said specimen input passage and defining a specimen opening likewise in alignment with said specimen input opening of said furnace tube; said second channel means including a gas channel which opens below the center of said furnace body so as to permit the external protective gas to distribute over the lower half of said furnace body and through said first gap in the directions of said tube axis and said contact axis with only a smaller portion passing through said first gap in the direction of the contact axis and a larger portion passing through said second gaps in the direction of said tube axis to reach the contact pieces in the upper half of said interior and then leaving said hollow body through said specimen opening of said funnel; and, said first channel means including a main channel which divides into first and second channels terminating in said first and second outlets, respectively, whereby respective components of said internal gas flow first reach corresponding ones of said cuvette windows and are guided toward the center of said furnace tube with the two components of internal gas dividing at corresponding ones of said third gaps in a defined ratio and each component dividing into an external component and an internal component and likewise leaving the hollow body via said specimen opening of said funnel with each of the internal components first passing through said specimen input opening of said furnace tube.

* * * * *